United States Patent
Wixforth et al.

(10) Patent No.: US 8,323,985 B2
(45) Date of Patent: Dec. 4, 2012

(54) MIXING DEVICE AND MIXING METHOD FOR MIXING SMALL AMOUNTS OF LIQUID

(75) Inventors: Achim Wixforth, Munich (DE); Christoph Gauer, Munich (DE)

(73) Assignee: Beckman Coulter, Inc., Brea, CA (US)

(*) Notice: Subject to any disclaimer, the term of this patent is extended or adjusted under 35 U.S.C. 154(b) by 0 days.

(21) Appl. No.: 13/269,449

(22) Filed: Oct. 7, 2011

(65) Prior Publication Data
US 2012/0028293 A1   Feb. 2, 2012

Related U.S. Application Data

(63) Continuation of application No. 10/474,420, filed as application No. PCT/EP02/03257 on Mar. 22, 2002, now abandoned.

(30) Foreign Application Priority Data

Apr. 9, 2001 (DE) .................................. 101 17 772

(51) Int. Cl.
*G01N 1/10* (2006.01)
(52) U.S. Cl. ........ 436/180; 436/174; 422/500; 422/502; 422/503; 422/504; 310/313 R; 310/313 A; 310/313 B
(58) Field of Classification Search ............... 422/63–67, 422/68.1, 127–128, 500, 502–504; 436/180, 436/174; 310/313 R, 313 A, 313 B
See application file for complete search history.

(56) References Cited

U.S. PATENT DOCUMENTS

| 4,280,823 | A |   | 7/1981 | Szonntagh |
| 4,575,485 | A |   | 3/1986 | Sizto et al. |
| 4,655,083 | A |   | 4/1987 | Chubachi |
| 4,735,906 | A |   | 4/1988 | Bastiaans |
| 4,767,719 | A | * | 8/1988 | Finlan .......................... 436/501 |
| 4,905,701 | A |   | 3/1990 | Cornelius |
| 5,006,749 | A |   | 4/1991 | White |
| 5,306,644 | A |   | 4/1994 | Myerholtz et al. |
| 5,632,957 | A |   | 5/1997 | Heller et al. |
| 5,639,423 | A |   | 6/1997 | Northrup et al. |
| 5,646,039 | A | * | 7/1997 | Northrup et al. ........... 435/287.2 |

(Continued)

FOREIGN PATENT DOCUMENTS

DE   19534955 A1   3/1996

(Continued)

OTHER PUBLICATIONS

Knight et al.; "Hydrodynamic Focusing on a Silicon Chip: Mixing Nanoliters in Microseconds"; Physical Review Letters; 80(17):3863-3866 (Apr. 1998).

(Continued)

*Primary Examiner* — Brian R Gordon
(74) *Attorney, Agent, or Firm* — Kilpatrick Townsend & Stockton LLP

(57) ABSTRACT

The invention relates to a mixing method for mixing at least one small quantity of liquid, in which a quantity of liquid is applied in a reaction region and at least one surface sound wave is reacted with the quantity of liquid. The invention relates further to a mixing device for mixing at least one quantity of liquid for performing the method of the present invention, a use of the device, and a method of analysis for bond strengths on surfaces.

41 Claims, 10 Drawing Sheets

U.S. PATENT DOCUMENTS

| | | | |
|---|---|---|---|
| 5,674,742 A | 10/1997 | Northrup et al. | |
| 5,736,100 A | 4/1998 | Miyake et al. | |
| 5,746,981 A | 5/1998 | Satoh | |
| 5,814,525 A | 9/1998 | Renschler et al. | |
| 5,910,286 A * | 6/1999 | Lipskier | 422/68.1 |
| 5,939,174 A | 8/1999 | Satoh | |
| 6,010,316 A | 1/2000 | Haller et al. | |
| 6,033,852 A | 3/2000 | Andie et al. | |
| 6,383,452 B1 | 5/2002 | Miyake et al. | |
| 6,440,725 B1 | 8/2002 | Pourahmadi et al. | |
| 6,664,104 B2 | 12/2003 | Pourahmadi et al. | |
| 6,719,449 B1 | 4/2004 | Laugharn et al. | |
| 6,723,516 B1 | 4/2004 | Tom-Moy et al. | |
| 6,737,021 B2 | 5/2004 | Watari et al. | |
| 6,773,676 B2 | 8/2004 | Schembri | |
| 6,773,677 B2 | 8/2004 | Thorne et al. | |
| 6,777,245 B2 | 8/2004 | Wixforth | |
| 6,852,284 B1 | 2/2005 | Holl et al. | |
| 7,169,601 B1 | 1/2007 | Northrup et al. | |
| 7,186,383 B2 | 3/2007 | Webster et al. | |
| 7,192,557 B2 | 3/2007 | Wu et al. | |
| 7,198,813 B2 | 4/2007 | Wixforth | |
| 7,297,313 B1 * | 11/2007 | Northrup et al. | 422/131 |
| 7,935,312 B2 * | 5/2011 | Northrup et al. | 422/138 |
| 2002/0141903 A1 | 10/2002 | Parunak et al. | |
| 2002/0176804 A1 | 11/2002 | Strand et al. | |
| 2002/0187560 A1 | 12/2002 | Pezzuto et al. | |
| 2003/0175947 A1 | 9/2003 | Liu et al. | |
| 2003/0198576 A1 | 10/2003 | Coyne et al. | |
| 2004/0087033 A1 | 5/2004 | Schembri | |
| 2004/0101975 A1 | 5/2004 | Gauer | |
| 2004/0180130 A1 | 9/2004 | Wixforth | |
| 2005/0106742 A1 | 5/2005 | Wahl | |
| 2006/0078473 A1 | 4/2006 | Murakami | |
| 2007/0098600 A1 | 5/2007 | Kayyem | |
| 2008/0156078 A1 * | 7/2008 | Hsieh et al. | 73/54.02 |
| 2009/0124513 A1 * | 5/2009 | Berg et al. | 506/9 |
| 2009/0280509 A1 * | 11/2009 | Lee et al. | 435/7.21 |

FOREIGN PATENT DOCUMENTS

| | | |
|---|---|---|
| DE | 10055318 A1 | 12/2001 |
| GB | 2293117 A | 3/1996 |
| JP | 01-177707 A | 7/1989 |
| JP | 6-50974 A | 2/1994 |
| JP | 7-508928 A | 10/1995 |
| JP | 2003-535349 A | 11/2003 |
| WO | WO 94/05414 A1 | 3/1994 |
| WO | WO 95/34374 A1 | 12/1995 |
| WO | WO 01/21291 A2 | 3/2001 |
| WO | WO 01/94017 A1 | 12/2001 |

OTHER PUBLICATIONS

Moroney et al.; "Microtransport Induced by Ultrasonic Lamb Waves"; *Appl. Phys. Lett.*; 59(7):774-776 (Aug. 1991).

Patent Abstracts of Japan, vol. 0134, No. 59, Oct. 17, 1989 (JP 01-177707; Jul. 14, 1989).

* cited by examiner

MIXING DEVICE AND MIXING METHOD FOR MIXING SMALL AMOUNTS OF LIQUID

This application is a continuation of U.S. patent application Ser. No. 10/474,420, filed Oct. 9, 2003 as the U.S. National Stage entry of International Application No. PCT/EP2002/003257, filed Mar. 22, 2002, which claims priority to German Application No. 101 17 772.0, filed Apr. 9, 2001; the disclosures of each are herein incorporated by reference in their entireties.

The invention relates to a mixing method, a mixing device for mixing at least one small quantity of liquid, a use for the device and an analytical method for bond strengths on surfaces.

The term liquid includes thereby other pure liquids, mixes, dispersions, and suspensions, as well as liquids, in which solid parts, for example, biological materials are located.

In microanalysis, small quantities of liquid must be mixed or stirred. R. M. Moroney et al describe in Appl. Phys. Letters 59, pages 774 and on (1991) the mixing of liquid in a 250 μm deep cavity with the use of an ultrasonic lambda wave, which disperses in a thin, flexible membrane, which closes off the cavity on one side.

Mixing processes for the smallest quantities of liquid were of value for specialized "lab-on-chip" technology since the earliest time point, which can be performed on a chip. The size of the quantity of liquid is in the range of pico- to milliliters. The relevant surfaces on the chip are in the millimeter, micrometer, or submicrometer range.

The mixing process of small quantities of liquid is essentially diffusion-driven. Since the typical reaction times of many chemical or biological process are very short, the necessary time for the chemical/biological process on the chip is determined essentially by the time of the mixing of the reactants.

For acceleration of the mixing, James B. Knight et al proposed in "Physical Review Letters" 1998, pages 3863 and on of driving a quantity of liquid with high speed on a chip in a 10 μm deep channel through a narrow point in a buffer solution. With a thin liquid jet produced in this manner, mixing is accelerated.

Also in the border region of such a laminar liquid stream, the mixing occurs, however, always still by diffusion.

Thus, it is desirable if homogenous reaction conditions can be produced in a quick manner, for example, concentration and temperature. Also, this can be achieved by mixing.

The object of the present invention is to provide a method and device with which mixing of one or more small quantities of liquid can be performed simply, cost-effectively, and effectively on the smallest space, for example, on a chip.

This object is resolved with a method with the features of claim 1 and a device with the features of claim 18. The respective dependent claims relates to advantageous forms. An analytical method for analyzing the bond strength on the surface with the use of the method of the present invention or an advantageous use of the device of the present invention are the subject matter of claim 44 or 43.

With the mixing method of the present invention, one or more small quantities of liquid are brought into a reaction region of a solid body surface, for example, a chip. There, it is brought to a reaction with at least one surface sound wave by mixing.

The size of the reaction region is in the range of millimeters, micrometers, or submicrometers. The amount of the liquid is adapted to this size.

The quantity of liquid and the sound path can completely overlap for maximum reaction effect. A partial overlapping makes possible the production of additional turbulence.

The surface sound wave transmits an impulse onto the quantity of liquid. This impulse transmission is achieved either by the mechanical deformation of the solid body surface by the surface sound wave and/or by the electrical field, which conducts the mechanical deformation with the use of piezoelectric substrates.

By the impulse transmission and by the restoring force determined by the surface tension of the liquid, a substantial turbulent flow is released into the liquid, which permits the chemical reaction to run substantially more quickly than in a pure diffusion situation.

Particular advantages of the impulse transmission by means of surface sound waves for manipulation of small quantities of liquid are:

1. The intensity of the action of force on the small quantity of liquid can be adjusted in a wide region via the amplitude of the surface wave.
2. Different temporal distributions of the force can be electronically defined in a simple manner, such as, for example, pulses of different lengths.
3. The exposure to sound waves of the solid body surface with the surface wave affects an automatic cleaning of the areas contacted.
4. A control via corresponding software is possible in a simple manner.

The surface sound wave can be produced with the assistance of a surface wave generating device, which is located in a known distance to the region in which the liquid is located on the solid body surface. The mixing is particularly efficient if the surface wave generating device is located directly in the region on which the liquid is applied. By the corresponding deformation of the surface or the force effect by means of the electrical field assisting the deformation, the liquid can be effectively and directly mixed.

With one form of the method of the present invention, the liquid quantity or quantities are applied in a depression of the solid body surface, which is small relative to the wave length of the surface wave. Such a depression makes possible the accurate localization of the quantity of liquid on the solid body surface.

With another form of the method of the present invention, the liquid is applied in a region of the surface, whose wetting characteristics are different from its lateral surrounding area, such that the liquid preferably is stopped there. With such a form, it is not necessary that the liquid is brought into a depression. On the surface region with the different wetting characteristics than its lateral surrounding area, the liquid quantity is retained, based on its surface tension. The liquid is located on this preferred holding region, for example, in the form of drops. Thus, it is particularly advantageous that in spite of the defined holding region of the liquid, which is achieved by modulation of the wetting characteristics, no trenches, corners, or edges are necessary, which could at least locally affect the mixing process. By means of the essentially planar surface, the application as well as the removal of the liquid is markedly simplified before and after the process. Also, cleaning of the surface is more simply performed than in the case of a depression.

With action of too large of an outer force, the quantity of liquid does not leave the depression or the preferred holding region based on its surface tension. First, with the effect of a sufficiently large force, the liquid is driven out from the region. With the method of the present invention, then, first with a minimal intensity of the surface sound wave, a blending of the liquid on the preferred holding region is can be achieved. Should the liquid leave this region, then, the intensity of the surface sound wave can be increases until the liquid leaves the preferred holding region.

The surface sound wave can be produced on the piezoelectric substrate or substrates with piezoelectric regions, for example, piezoelectric coatings. Thus, it can be achieved than the substrate or corresponding coatings are present only in the region in which the surface wave generating device is located.

The surface wave can be continuously emitted, in order to provoke the mixing process. It is particularly effective, however, when the surface sound wave is pulsed.

If, in addition, the pulse frequency of the surface sound wave is selected, such that it is the same as a eigenfrequency of a small quantity of liquid, a resonance excess occurs, which still further intensifies the mixing. The pulse frequency suited for this purpose is based on the quantity of liquid or its volume and its surface tension and amounts typically to a few HZ up to a few kHz.

The surface sound wave can be emitted, for example, such that the quantity of liquid is uniformly exposed to sound waves. Beneath the quantity of liquid, the solid body surface deforms by the permeating surface sound wave and thus forms a mechanical deformation. This mechanical deformation or the electrical field assisting it acts on the quantity of liquid in the border region between the quantity of liquid and the solid body-surface. The running surface wave moves with the lower part of the quantity of liquid. Based on the surface tension, with a sufficiently minimal intensity of the surface sound wave, the quantity of liquid nevertheless does not leave the preferred holding region or the depression. In order to produce a volume equalization within the quantity of liquid, a counter flow forms in the upper area of the quantity of liquid, which is removed from the solid body surface. In this manner, a movement in the quantity of liquid is produced and a stirring or blending is achieved.

With another embodiment, the surface sound wave is sent decentrally onto the quantity of liquid. The quantity of liquid is impinged then only in a partial area and begins to rotate, for example.

A similar effect can be achieved when the surface sound wave is generated by a surface wave generating device, which is located in the preferred holding region or in the depression, however not symmetrical thereto.

With another embodiment of the method of the present invention, at least two surface sound waves are sent onto the quantity of liquid, which are phase-displaced in the region of the quantity of liquid. For example, two parallel surface sound waves with a phase-displacement of a half wavelength can be sent onto the quantity of liquid. The impulse transmission, which is transmitted by the "wave peaks" of the surface sound wave onto the quantity of liquid, is then likewise phase-displaced, so that a formation of vortices in the quantity of liquid occurs, which affects a very effective stirring or blending.

The phase-displacement can achieve that two parallel arranged surface wave generating devices with a corresponding phase-displaced frequency are controlled. Likewise, the surface wave generating devices can have a different distance from the reaction region, which does not correspond to the whole-number multiple of a wave length.

With a further advantageous form of the method of the present invention, the liquid is brought into a surface region, in which a resonator for a surface sound wave is located, which, for example, is produced with a spaced surface wave generating device. Such a resonator can be produced, for example, by a periodically etch structure or periodically applied coating, preferably made of metal. A surface sound wave, which runs in this region, is amplified locally, in order to stimulate the mixing process in the liquid.

For effective production of turbulences, in the preferred holding region or in the depression, in which the liquid is located when performing the method of the present invention, interference elements can be applied, which stimulate the formation of turbulences.

For production of the surface wave, with one advantageous form, a known interdigital transducer is used. Such an interdigital transducer, for example, has two electrodes, which engage in one another in the manner of fingers, for example, at distances of a few µm. By application of a high frequency alternating field, for example, in the dimension of a few MHz up to a few 100 MHz, a surface sound wave is stimulated in a piezoelectric substrate or in a piezoelectric region of the substrate, when the resonance condition at least is approximately fulfilled that the frequency is the same as the quotient from the surface speed and the finger distance of an electrode. The dispersion direction is perpendicular to the engaged finger electrode structures. Of course, also other interdigital transducer geometries can be used, such as those known from the technology of surface wave filters. With the assistance of an interdigital transducer, a very defined surface sound wave can be produced in a very simple manner. The manufacture of an interdigital transducer is cost-effective and simple with known lithographic methods and coating technologies. Interdigital transducers can be wirelessly controlled, for example, by radiation of an electromagnetic alternating field in an antenna device connected with the interdigital transducer.

The method of the present invention is suited for the stirring of a quantity of liquid, in order to provoke a reaction therein and/or to create homogenous conditions, for example. The term "mixing", then, also should include a stirring in the sense of an agitation process. Likewise, the method of the present invention can be used to mix two or more liquids with one another. Also, in this case, the speed of the mixing or the reaction is not limited by diffusion.

The method of the present invention likewise can be used advantageously in order to release solids, such as a powder-type material into a liquid. The powder first is applied onto the reaction region of the solid body surface. In this connection, a liquid is applied and with the assistance of the surface sound wave, a turbulent movement is produced. Thus, the release of the powder-type material is accelerated and a mixing can take place very quickly.

A further advantageous form of the method contemplates that during the mixing process, additionally at least locally heat is applied, in order to intensify the mixing process and the production of the turbulence current further.

The mixing device of the present invention for performing a method of the present invention includes at least one reaction region on a solid body surface and at least one surface wave generating device, which is arranged on the reaction region such that energy of a surface sound wave generated by it is transmitted to the quantity of liquid, which is located in the reaction region.

With the term solid body surface, in the frame of the subject matter of the present invention, either the surface of a solid body, for example, of a chip, such as those known from semi-conductor technology, is intended or a coating on a solid body surface, for example, a metallic coating or an insulating coating. Likewise, for example, a quartz layer on a solid body should be understood as a solid body surface. Likewise, the invention includes embodiments, in which a part of a solid body surface, for example, of a piezoelectric lithium niobate crystal, is provided with a coating, for example, quartz.

With one form of the device of the present invention, a depression is provided on the solid body surface. A surface wave generating device is arranged on the solid body surface, such that it can produced a surface sound wave, which can impinged with a liquid into the depression in a reaction. The lateral extension of the depression is determined according to the quantity to be manipulated. Typically, amounts here are a few micrometers to millimeters.

If the surface wave generating device is arranged outside of the depression, then the depression should be small relative to the wave length, which can be generated with the surface wave generating device. Typically, this is a few micrometers. With a deeper depression, a surface wave, which is produced by a surface wave generating device outside of the depression, cannot overcome the step for entry into the depression.

With another form of the present invention, the surface wave generating device is provided within the region of the depression itself, so that no limitation for the depth of the surface wave generating device is necessary. Such an arrangement makes possible also the effective mixing of a liquid within the depression, since the surface wave can be directly reacted with the quantity of liquid.

If necessary, the surface sound wave generating device is provided with a coating, in the vent the material of the surface wave generating device for the liquid to be analyzed or the material located therein could be damaging. This coating is selected, such that the surface sound wave still can affect on the liquid. The thickness of the coating in the reaction region must be smaller than the surface sound wave length.

With another form of the device of the present invention, in the region of the surface wave generating device, the surface characteristic of the solid body surface is selected, such that the wetting characteristics of this region differ from the lateral surrounding area, in that the quantity of liquid preferably is retained or stopped there. Also, with such a form of the present invention, the surface sound wave generating device is arranged in the region of the preferred holding region, in order to most effectively form the reaction between the surface sound wave and the quantity of liquid on the preferred holding region. Depending on the material of the surface sound wave generating device and a possible coating for the preferred holding region, again a sufficiently thin additional protective layer can be provided between these elements or on these elements, in order to separate the liquid from these elements.

For modulation of the wetting characteristics, for example, hydrophilic or hydrophobic regions can be used. Should aqueous solution be manipulated, the preferred holding region is selected, for example, such that it is more hydrophilic than the surrounding solid body surface. This can be achieved either by a hydrophilic coating of the preferred holding region or by a hydrophobic surrounding area. A hydrophobic surrounding area, for example, with a preferred form of the invention can be realized through a silanization of the surface.

Depending on the use, the solid body surface surrounding the holding region can be hydrophilic, lipophobic, or lipophilic in comparison to the surface of the holding region. For manipulation of a non-aqueous solution, for example, it can be advantageous if the preferred holding region is lipophilic in comparison to the surrounding area.

The modulation of the wetting characteristics can be achieved, for example, by a corresponding coating.

The definition of the preferred holding region, in which the liquid is more intensely wetted than in its surrounding area, also can take place or be supported by a flat etching of the surface in this area, whereby the etching depth is small relative to the lateral extension of the preferred holding region, for example, one-tenth of its lateral extension. Thus, for example, in the case of an aqueous solution, the preferred holding region is defined, in that the surface surrounding the preferred holding region is coated hydrophobically and etched in a few nanometers to a few micrometers in the surface in the area of the holding region itself. In this manner, the contrast with reference to the wetting angle of contact is increased. Nevertheless, the surface macroscopically is planar. Such a flat etching, in addition, is very simply and definitely manufacturable in production technology, without the known problems of deep etching occurring. The wetting characteristics can be further modulated by micro-structuring, such as is the case with the so-called Lotus effect, which contacts on the different roughnesses of the surfaces. This can be obtained, for example, by micro-structuring of the corresponding surface regions, for example, by chemical treatment or ion radiation. The making of regions with different wetting characteristics is simply and cost-effectively performed, then, with the aid of already known lithographic methods and coating technologies.

The surface wave generating device can be located on the region with modulated wetting characteristics or on the surface of the depression. In particular, it is advantageous when a coating is provided above the surface wave generating device, which, for example, is biocompatible. With the assistance of such a coating, an influence on the liquid by the material of the surface wave generating device can be prevented or damage of the surface wave generating device by the liquid can be prevented, when it operates, for example, as an etching liquid.

With the choice of a biocompatible coating, for example, biological materials are analyzed in a buffer solution, without an impending adverse effect or damage of the material or negative affecting the reaction conditions. A possible material for a biocompatible coating is silicon dioxide, for example.

In this connection, also a biocompatible coating, for example, made from silicon dioxide, can be provided on the solid body surface, in which a depression is etched, which should receive the liquid. The surface sound wave generating device can be arranged in a region of the surface, on which no silicon dioxide is located. The surface sound wave disperses from the surface sound wave generating device to the solid body surface also in the region in which the silicon dioxide is located. Such a silicon dioxide layer can be very easily etched, in order to produce a defined depression. Thus, the surface sound wave can be reacted with the liquid in the depression, should the thickness of the biocompatible coating in the area of the depression be small relative to the wave length of the surface sound wave.

It is particularly simple if the coating is selected, such that it also has wetting characteristics, which differ from the lateral surrounding area, such that the liquid preferably is stopped or retained there.

With an advantageous further embodiment of the mixing device of the present invention, interference elements are provided in the reaction region. With one form with a preferred holding region, these interference elements, for example, exist in an irregular definition of this holding region. A liquid, which moves onto the holding region based on the action of a surface sound wave, is displaced by the reaction with the irregular edge into turbulence. A similar effect can be produced by an irregular depression.

Also within the reaction region, turbulence-producing interference elements can be provided. With an embodiment with a depression, these interference elements can be produced, for example, by vertical elements, which have been left with the etching process for production of the depression. With an embodiment with a preferred holding region, which is defined by the different wetting characteristics, such interference elements can be defined by regions within the preferred holding region, which have wetting characteristics that are selected, such that the liquid does not wet as well with the surface of the interference elements as with the surrounding preferred holding region.

A simple embodiment of the device of the present invention includes one or more interdigital transducers for production of the surface sound waves.

In order to make possible an additional heating of the liquid to be mixed, a heating device, for example, a resistance heating, can be provided in the region of the depression or in the preferred holding region defined by the modulation of the wetting characteristics.

A resonance excess can be achieved, when a resonator is located within the depression or the preferred holding region, which is positioned, such that s surface sound wave, which is produced with the surface wave generating device of the device of the present invention, resonates. With an embodiment with an interdigital transducer as the surface sound wave generating device, such a resonator can comprise, for example, periodic metallic strips, whose distance is commensurable with the finger arrangement of the interdigital transducer for production of the surface waves. With another embodiment, such a resonator can have etched strips, for example, or other coatings in the corresponding geometry.

As a special feature for the application for conductive quantities of liquid, a coating of the resonators and/or surface wave generating devices is advantageous. If a conductive medium is located in a distance to the surface wave generating device, which is smaller or the same as the wave length of the surface sound waves, then the electrodes of the surface wave generating device are capacitively coupled, whereby the efficiency with which the surface wave generating device converts electrical energy into acoustic energy, and with it, also the mixing efficiency, is reduced. If one provides the surface wave generating device and/or the resonators with an insulating layer, the mixing efficiency can be increased, since the evanescent, electrical field exponentially drops. In particular, a coating with a high dielectric constant is advantageous, since then the electrical field drops out particularly quickly. With a particular form, the layer is selected to be so thin that its thickness is smaller or approximately the same as the wave length of the surface sound waves produced with the surface sound wave generating device. A thicker coating would intensely dampen the surface sound waves mechanically and again reduce the mixing efficiency. The coating can be organic, for example, made from photoresist, or inorganic, for example, silicon dioxide or silicon nitride. The coating can be applied with known methods, such as by spraying or spinning. For biological applications, the coatings again preferably are biocompatible. Further, the coatings can be laterally structured.

The device of the present invention can be part of a total system. For example, multiple "mixing chambers" of such a type can be provided on a single solid body chip, in order to perform multiple processes at the same time. Likewise, a mixing device of the present invention can be part of a complex system with multiple analytical or synthesis devices, which makes possible other analytical or synthesis steps. In a simple manner, a "lab-on-a-chip" can be realized, on which multiple, different processes can be performed simultaneously. For production of the surface sound waves for a mixing device, one or more surface wave generating devices can be provided at the same time, which, for example, can be operated with different intensities.

Filling of the mixing device for performing the method of the present invention can take place with the aid of a pipette robotics, for example. Likewise, it can be provided that channels or lines are provided, which have wetting characteristics similar to the preferred holding region, which differ from its lateral surrounding area, such that the liquid preferably stops thereon. A quantity of liquid can be moved along such a line, for example, by impulse transmission of a surface sound wave.

The invention is not limited to individual, free solid body surfaces. Likewise, the invention can be realized in arrangements, in which two solid body surfaces face one another, between which a quantity of liquid is located. With such an embodiment, the depression defining the reaction region or the preferred holding region defining the reaction region can be located on one surface and the surface wave generating device can be located on the opposite surface. With such an arrangement, likewise the advantageous effects of the present invention can be achieved, when the small quantity of liquid comes into contact with both surfaces. With such an arrangement, the preparation steps for making the surface wave generating device and the preferred holding region or the depression can be performed independently from one another, before the surfaces are arranged opposite one another.

An analytical method for analyzing the bond strength of objects is also provided by the present invention. The above-described mixing method of the present invention for mixing small quantities of liquid is used with a solution with microscopically small objects. During or after the reaction of this solution with the surface sound wave, depending on the current, which is produced by the surface sound wave, the amount or number of the objects adhered to the surface is analyzed or counted. The mixing device of the present invention, then, is also used in order to produce turbulent currents, for example.

After the solution drop is placed on the surface, where it is held together by its surface tension, the microscopically small objects sink onto the surface. There, they can adhere either by a specific or non-specific bond or adhesion. The solution drop is displaced into movement with the surface sound wave according to the mixing device of the present invention. Depending on the current speed or strength of the surface sound wave, the microscopically small objects located on the surface can be carried away and thus removed. If the quantity of the objects adhered to the surface depending on the current speed or strength is determined, a conclusion about the bond strength can be arrived at. A particular advantage of the use of surface sound waves is that the amplitude or the current speed can be adjusted in further regions, in particular, when interdigital transducers are used for production of the surface sound waves.

Particularly advantageously, this method can be used when a nutritive solution is used as the quantity of liquid and biological objects, in particular, cells or bacteria, are analyzed. If necessary, the surface can be functionalized totally or in partial regions, in order to analyze the bond strength on different functionalized surfaces.

The functionalizing can include, for example, cellular mono-layers or a coating with adhesion molecules. The cellular coating, for example, can comprise endothelial cells. The adhesion molecules, for example, can be isolated from endothelial cells or extra-cellular matrix proteins, such as fibronectin.

If different functionalizings are provided in different regions on a surface, different bonds can be analyzed in parallel on one surface. In addition, different local examples of current can be realized on one chip, for example, by different transducers, in order to selectively control different functionalized regions, for example.

A particularly advantageous use of the mixing device provides for a cell adhesion assay, which serves for analysis of the bonding of cells on functionalized surfaces. Since cells sink in a nutritive solution and adhere non-specifically to the substrate surface, it is important to distinguish specific bonds from non-specific.

With the mixing device of the present invention, the cells can be flowed against with a surface sound wave and again are analyzed, if individual cells break away as a function of the current speed. In this manner, the bond strength can be analyzed as a function of the current speed.

Cells with diameters of 10 to 100 μm, for example, sit counter to the current induced with the surface sound wave in the event, for example, of a non-specific bond on the surface of a sufficient resistance, such that the bond between the surface and object can be broken by the current.

The invention will be described in detail with reference to the accompanying figures. The figures show schematic drawings, which are not necessarily drawn to scale. In the figures:

FIG. 1b shows a lateral sectional view of the embodiment of FIG. 1a;

FIG. 2b shows a lateral sectional view of the embodiment of FIG. 2a;

FIG. 3b shows a lateral sectional view of the embodiment of FIG. 3a;

Figure 1A:
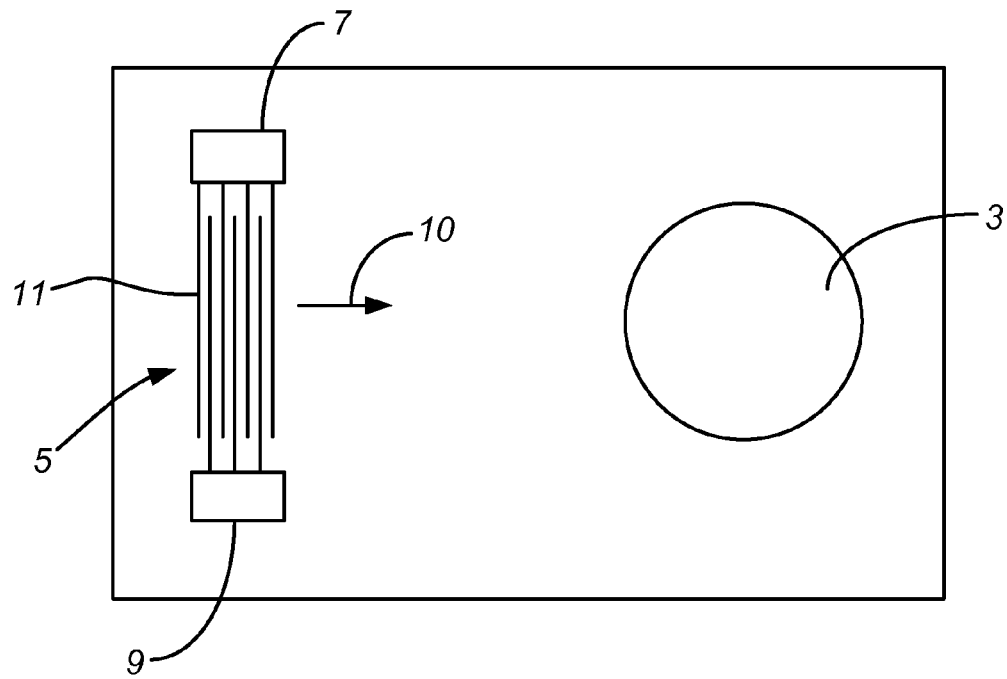
FIG. 1a shows a cut-out of an embodiment of the device of the present invention for performing the method of the present invention in plan view.
Figure 1B:
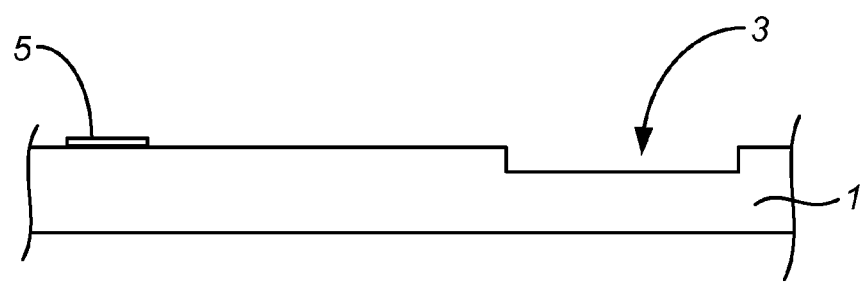

FIG. 1 shows in plan view (FIG. 1a) and in schematic sectional view (FIG. 1b), one embodiment of the device of the present invention. The shown cut-out from a chip surface has the order of magnitude of a few millimeters. On a solid body surface, whose, cut-out in FIG. 1a is visible, a depression 3 that is a few micrometers deep is provided. An interdigital transducer 5 is adjacent thereto on the solid body 1. The interdigital transducer 5 includes in the known manner electrodes 9 and 7, which include finger-type appendages 11, which engage in one another in distances of a few micrometers. The solid body 1 is a piezoelectric crystal, for example, lithium niobate. Alternatively, a non-piezoelectric solid body with a piezoelectric coating, for example, zinc oxide, can be provided.

The interdigital transducer 5 of the shown embodiment comprises electrodes 7 and 9 with finger-type electrode structures 11 engaging in one another. The finger-type electrode structures and the electrodes 7 and 9 can be lithographically defined, for example, and could be damped as a metallic coating. The layer thickness amounts, for example, to several 100 nanometers up to several micrometers. The thicknesses are shown in FIG. 1b, as well as in the other figures, as not true to scale. In the figures, the finger-type electrode structures engaged in one another are only shown schematically. Actually, a transducer includes, if necessary, a much larger number of finger electrodes engaged in one another.

With application of an alternating current on the electrodes of the interdigital transducer a surface sound wave is produced, whose frequency is provided as the quotient from the surface sound wave-speed and the finger distance. The wave length corresponds thereby in a known manner to the finger distance between two adjacent fingers of an electrode. The radiation direction of the surface sound wave is perpendicular to the connection line between the electrodes 7 and 9. The radiation of interest here is designated with 10. The electrical alternating field can either be applied over supply lines (not shown) to the electrodes 7 and 9, or with the assistance of an antenna device connected to the electrodes, can be radiated wirelessly.

Such a device of the present invention is used as follows:

A liquid to be mixed or the liquids to be mixed are, for example, applied with a pipette robotic into the depression 3. With the assistance of the interdigital transducer 5, a surface sound wave with the radiation direction 10 is generated. This surface sound wave acts on the quantity of liquid in the depression 3 and produces there a turbulent movement by means of the deformation of the solid body surface, which leads to mixing. With charged or polarizable material in the liquid, additionally an impulse transmission of the surface wave is produced by the electrical field, which accompanies the mechanical deformation of the surface in the piezoelectric crystal.

Figure 2A:
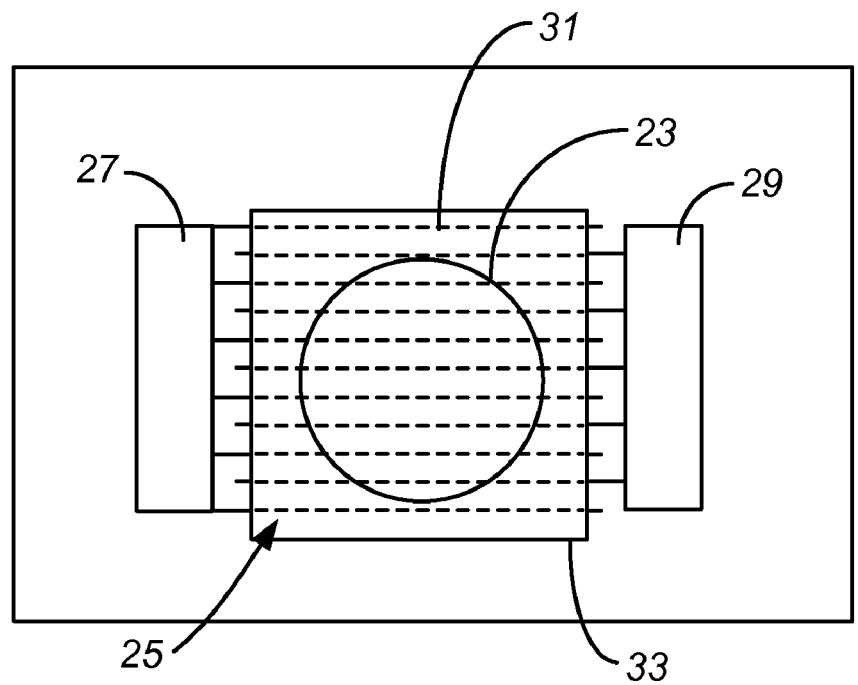
FIG. 2a shows a cut-out of a further embodiment of a device of the present invention for performing a method of the present invention in plan view.
Figure 2B:
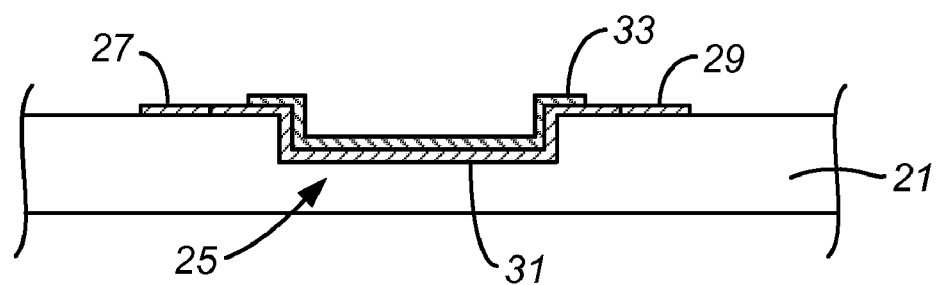

FIG. 2 show a further embodiment of the present invention. Again, FIG. 2a shows a plan view and FIG. 2b shows a schematic sectional view.

On the surface of the depression 23, an interdigital transducer 25 with electrodes 29 and 27 is located, which have finger-type appendages 31. The finger-type appendages extend into the depression 23, while the electrodes 27 and 29 are arranged outside of the depression with the shown embodiment. Reference numeral 21 designates in the figure, again, the piezoelectric substrate.

Above the interdigital transducer 31, a coating 33, for example, of silicon dioxide, is provided at least in this region, which, for example, represents a biocompatible protective layer.

Also, with the embodiment of FIG. 2, the liquid to be mixed is applied in the depression 23. The biocompatible protective layer 33 prevents the liquid from coming directly into contact with the metallic electrode structure of the interdigital transducer 25. If the liquid operates as a liquid with biological material, damage to the biological material is prevented by the silicon dioxide.

In this connection, as with the above-illustrated first embodiment, an electrical alternating field of a few MHz to a few 100 MHz is applied to the interdigital transducer 25, in order to produce a surface sound wave for deforming the surface. In the region of the interdigital transducer 25, the intensity of the surface sound wave is very intense and leads in this manner again to an effective mixing via the deformation of the solid boy or via the electrical action of force on charged or polarizable material.

Figure 3A:
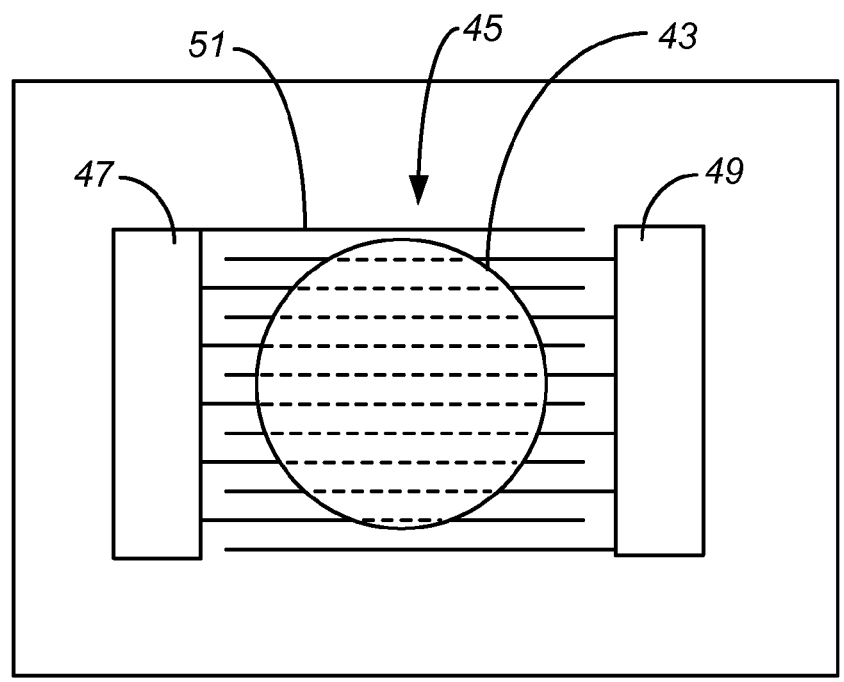
FIG. 3a shows a cut-out of a third embodiment of the device of the present invention for performing a method of the present invention in plan view.
Figure 3B:
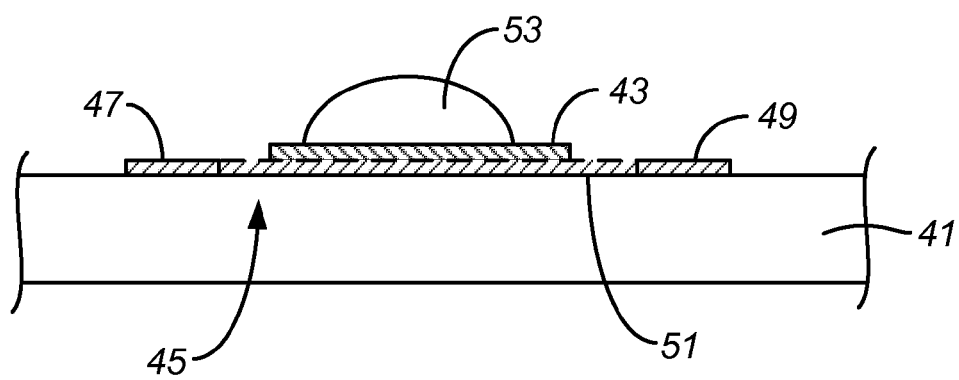

A further embodiment of the present invention is the subject matter of FIG. 3, in which, again, FIG. 3a shows a schematic plan view and FIG. 3b shows a cross sectional view. This embodiment has no depression. On the solid body 41, the interdigital transducer 45 is provided with electrodes 47 and 49, which again have finger-type, electrode appendages 51 engaged in one another. With the shown embodiment, a coating 43 is disposed above the interdigital transducer, which is selected, such that the liquid to be manipulated or the liquids to be manipulated preferably are stopped thereon. The coating 43 is selected, such that it is more heavily wetted by the liquid than the lateral surrounding area.

Alternatively, it can be provided that the surrounding area of a region, in which the interdigital transducer 45 is located, has wetting characteristics, such that the small quantity of liquid preferably is stopped there less than on the region, in which the interdigital transducer 51 is provided. For manipulation of aqueous liquids, the surrounding region is hydrophobic in comparison to the region, in which the interdigital transducer 45 is located. Hydrophobic wetting characteristics are achieved, for example, by silanizing of the surface.

With such an embodiment with a silanized surrounding area, however, additionally a coating 43, for example, of silicon dioxide, can be provided, in order to protect the interdigital transducer or to ensure biocompatibility.

For example, aqueous liquids are applied on the region with the interdigital transducer 45. Application of an electrical alternating field likewise affects an impulse transmission of a surface sound wave on the quantity of liquid 53, as with the embodiment of FIG. 2. In this manner, also with this embodiment, the mixing is effectively supplied.

The method of the present invention can be performed with a device according to FIG. 1, in which the depression 3 is replaced by a preferred holding region, whose wetting characteristics are selected in the manner described with reference to FIG. 3, such that the small quantity of liquid preferably is stopped or held thereon.

Figure 4:
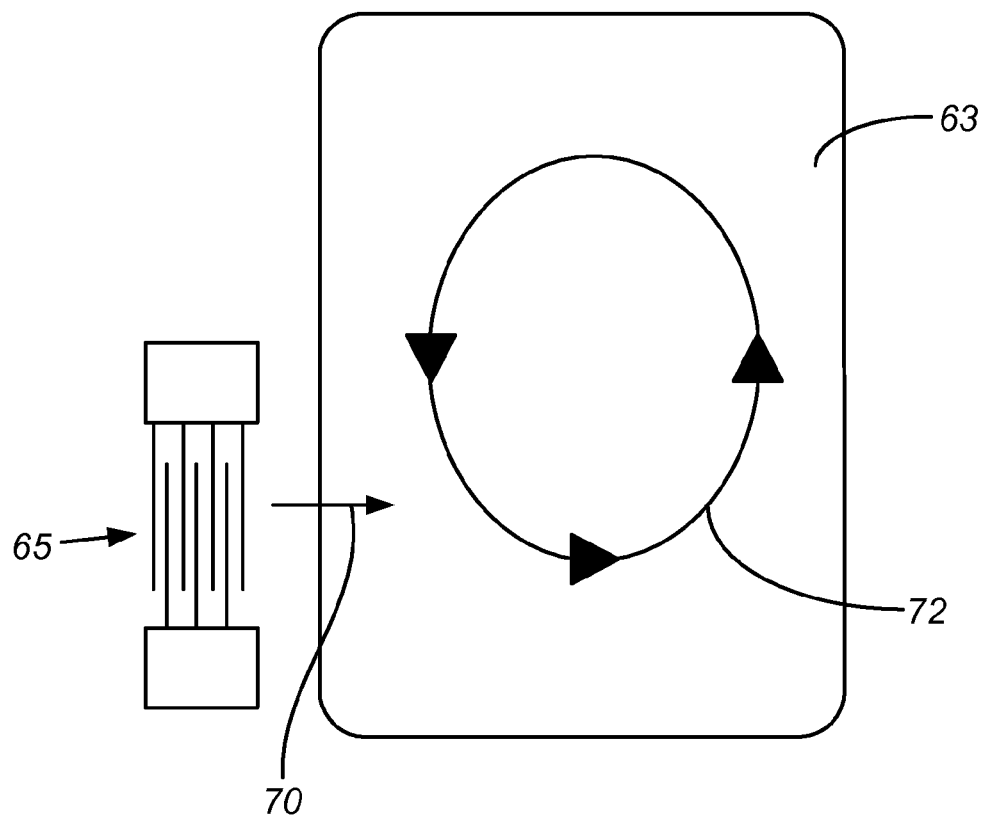
FIG. 4 shows a cut-out of a fourth embodiment of the device of the present invention for performing the method of the present invention in plan view.

In FIG. 4, an embodiment of the present invention with a preferred holding region 63 is shown, which, for example, is produced by the modulation of the wetting characteristics in a manner already described. A transducer 65, which, for example, corresponds to the above-described transducer 5, is arranged on the solid body surface, such that the wave path 70 acts decentralized on the preferred holding region 63 with the produced surface sound wave.

In the preferred holding region 63, a quantity of liquid is located, which is not shown in the figure. If a surface wave is produced with the transducer 65, then this widens in the direction 70 and acts decentrally on the quantity of liquid. If the intensity of the surface sound wave is sufficiently minimal, then the quantity of liquid is not removed by the impulse of the surface sound wave from the preferred holding region 63. By means of the impulse transmission, however, a movement within the quantity of liquid is produced, which leads to turbulence corresponding to the current profile 72. Thus, an effective mixing is achieved.

Figure 5A:
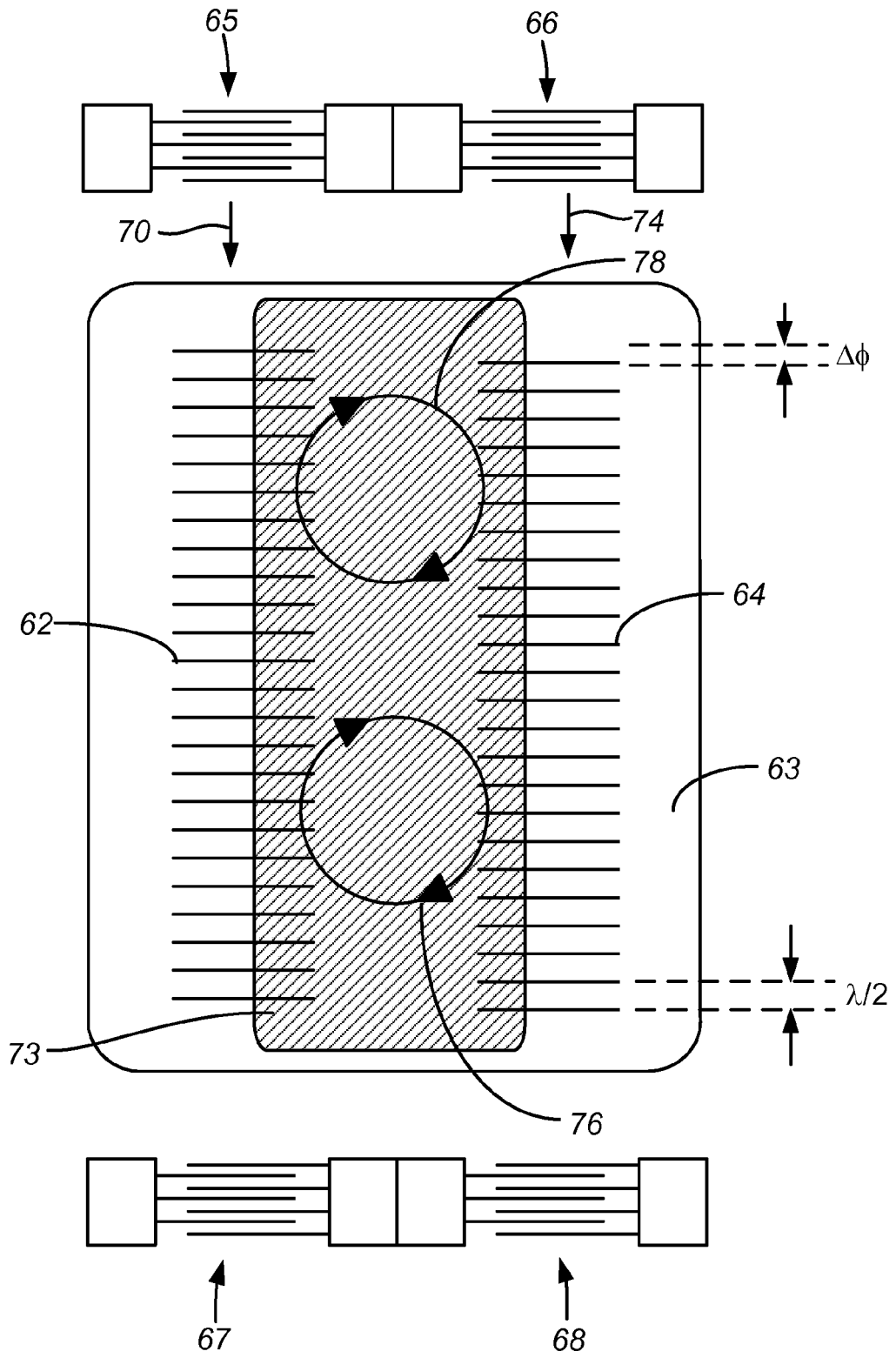
FIG. 5a shows a cut-out of a fifth embodiment of a device of the present invention for performing the method of the present invention in plan view.

With the embodiment of the present invention shown in FIG. 5a, two transducers 65 and 66 are provided, which, respectively, have a wave path 70 or 74, which acts decentrally on the preferred holding region 63.

Exemplary "wave peaks" of surface sound waves are designated with 62 or 64, which are produced with the transducers 65 or 66, when a phrase-displaced alternating current of the same frequency is applied to this. The phase displacement between the surface sound waves is designated with $\Delta\Phi$. Reference numeral 73 designated by way of example a quantity of liquid. The surface waves impinge transversely on the quantity of liquid 73. By the phase displacement, vortices are produced, which are designated by way of example with 76 and 78.

In FIG. 5a, optional further transducers 67 and 68 are provided, with which, respectively, a surface sound wave can be produced, which acts counter to the surface waves of the surface wave generating device 65 or 66. In this manner, a higher flexibility with the application is provided. With a suitable selection of the phase between the opposite transducers 65 and 67, also a continual surface wave can be stimulated, which can affect an intense mixing in the region between its nodes.

A similar effect can be achieved when the interdigital transducers are arranged on the chip surface with different distances to the preferred holding region. By the different running times of the surface sound waves, in this manner, a phase displacement between the surface waves can be achieved, which can are produced with the interdigital transducers.

Figure 5B:
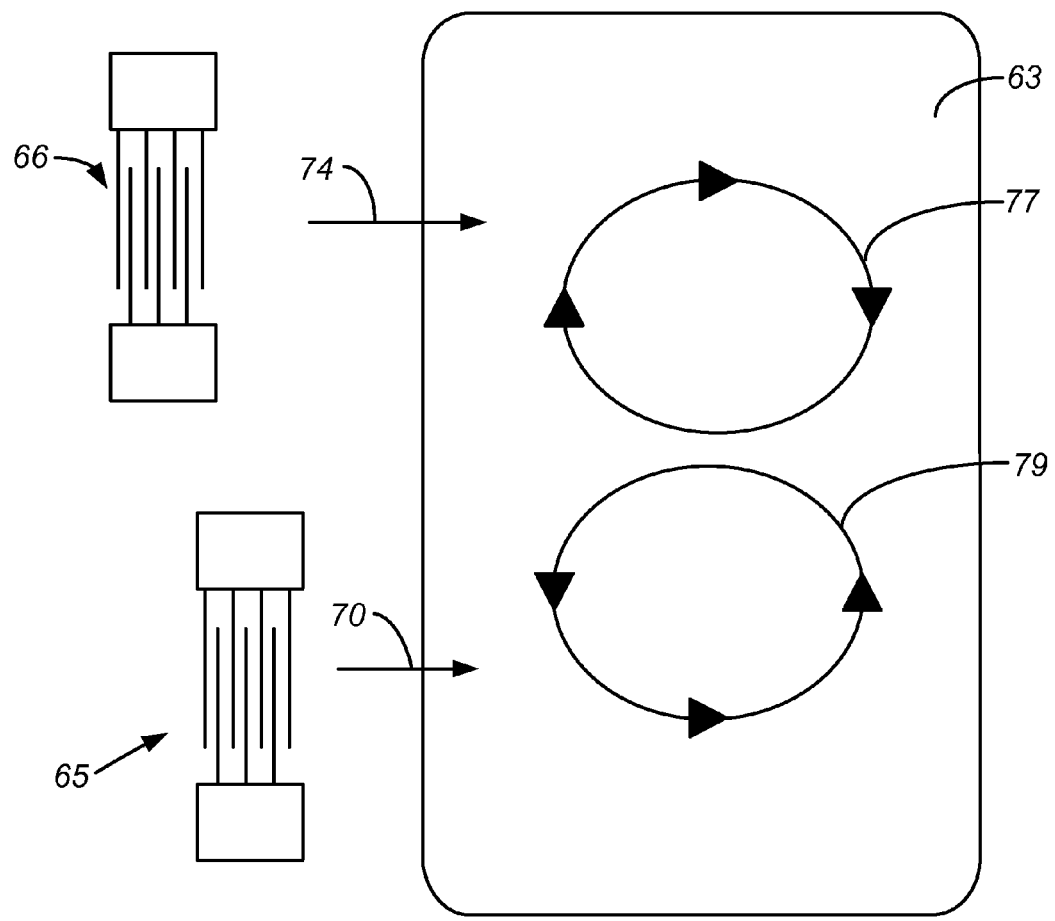
FIG. 5b shows a modification of the form shown in FIG. 5a of the method of the present invention.

FIG. 5b shows a modification, in which, likewise, two transducers are used in order to produce turbulence. The surface sound waves with the wave path direction 70 or 74 produced with the transducers 65 or 66 impinge decentrally on the preferred holding region 63, on which one of the quantity of liquids, which is not shown for purposes of clarity, is found. If the transducers 65 and 66 are stimulated by means of an alternating field, whose phase correlation is such that at the location of the holding region 63, the surface sound waves produced with the transducers 65 or 66 are in phase, thus forming the vortices designated with 77 and 79 in a quantity of liquid, which is located on the holding region 63 of FIG. 5b. Also here, an effective mixing of a quantity of liquid on the preferred holding region 63 is achieved.

Figure 6:
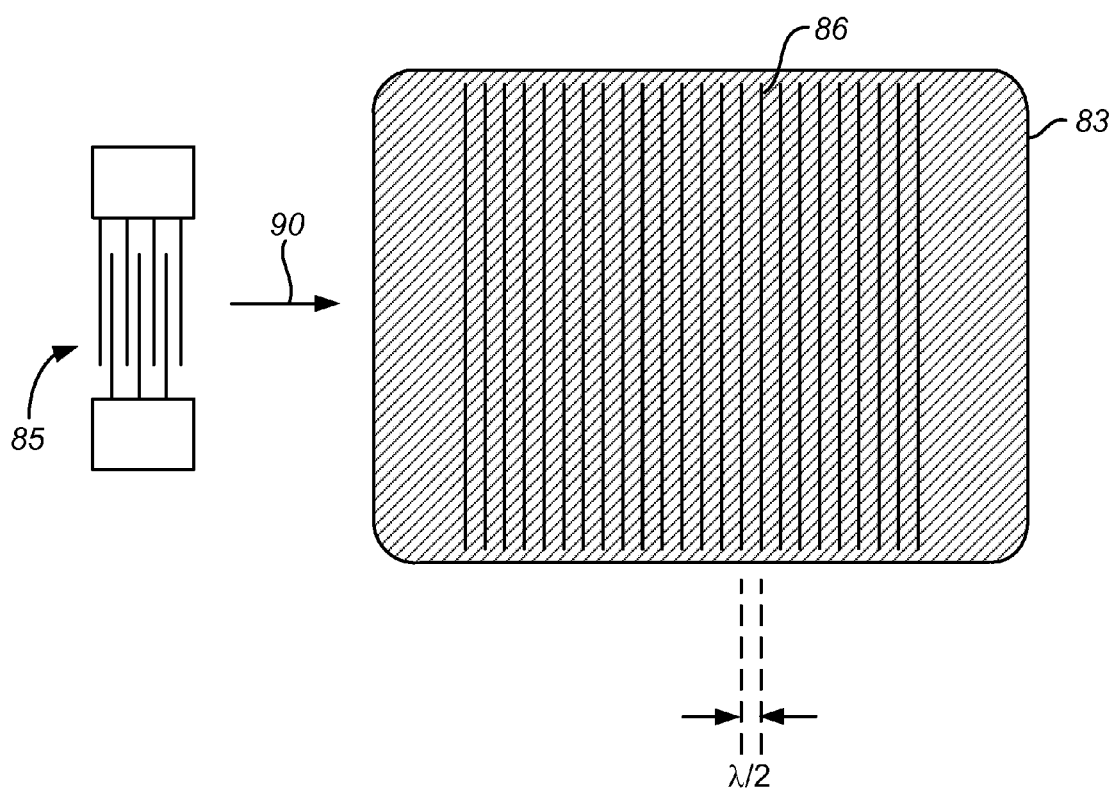
FIG. 6 shows a cut-out of a sixth embodiment of the device of the present invention for performing the method of the present invention in plan view.

In FIG. 6, an embodiment of the present invention with a resonator is shown. Reference numeral 85 designates again an interdigital transducer corresponding to the transducer of the embodiment of FIG. 1. Reference numeral 83 designated a preferred holding region, which, for example, would be produced again by modulation of the wetting characteristics relative to the surrounding regions of the solid body. In the preferred holding region, a resonator is arranged. This corresponds, for example, to a finger-type metal coating with a finger distance of half the wave length, which a surface wave has, which can be radiated in the direction 90 from the interdigital transducer 85, when an alternating field is applied to this. A strip of this metal coating is designated with 86, by way of example. Alternatively, for example, a periodic channel etching can be provided.

The resonator strips preferably are arranged at a distance of the half wave length and form discontinuity in the acoustic impendence of the free surface. On a piezoelectric substrate, also a discontinuity of the electrical edge characteristics positively occurs in addition to the discontinuity of the mass coating of the strips. A metal as the resonator on the surface of a piezoelectric mechanism additionally minimizes the wave speed beneath the metal, based on the short-circuiting of the piezoelectric field.

Such a resonator increases the surface sound wave amplitude at the location of the mixing in the preferred holding region. In such a resonator, with the radiation of a surface sound wave, a local, excess standing wave field is formed, which develops by phasecorrect reflections on the individual, periodically arranged discontinuities.

The resonator strips can be insulated from the preferred holding region by an intermediate layer. Likewise, on the resonator, a coating can be provided, which serves to protect the quantity of liquid located thereon. For the sake of clarity, these types of embodiments are now shown in FIG. 6.

Figure 7A:
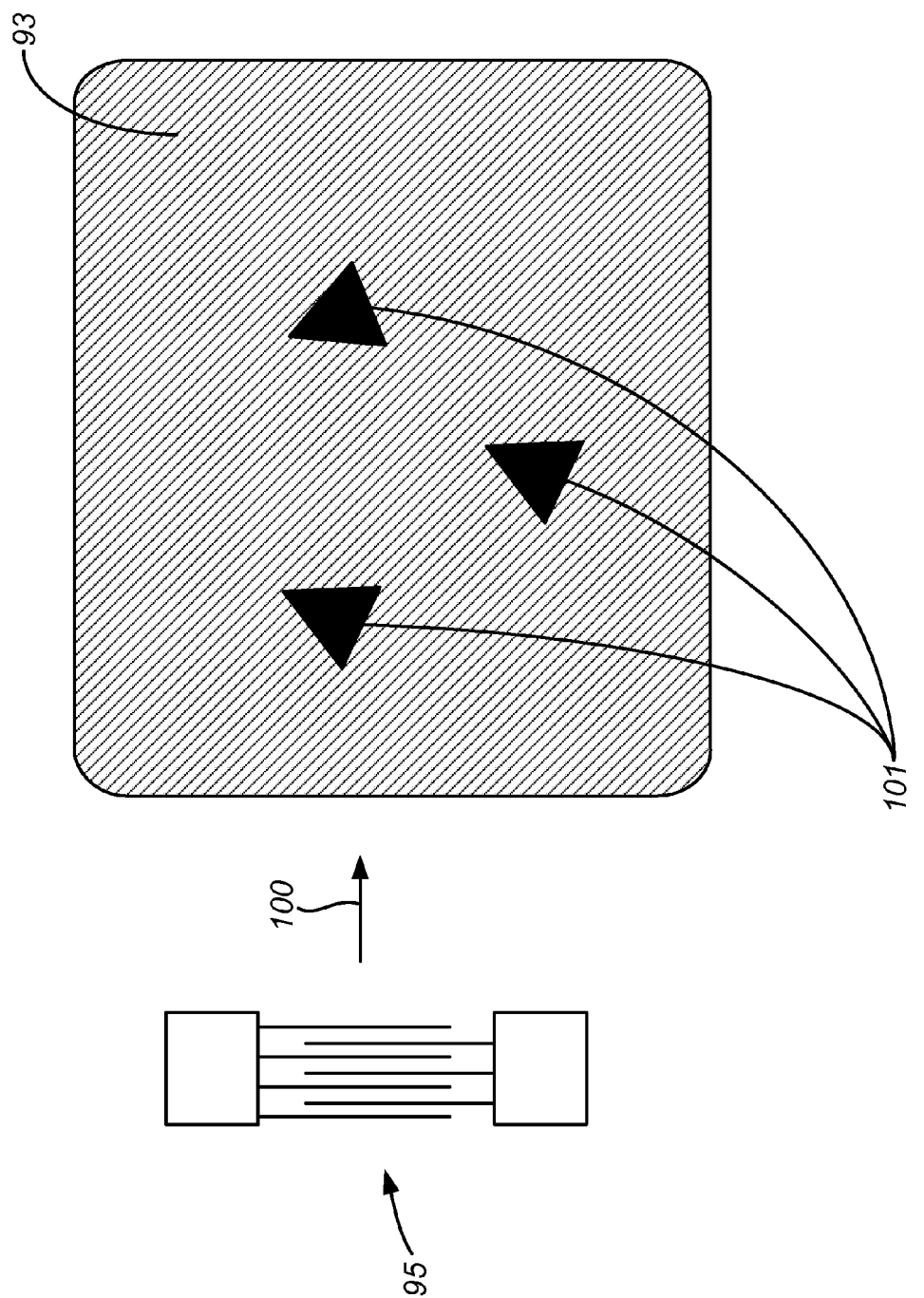
FIG. 7a shows a cut-out of a seventh embodiment of the device of the present invention for performing the method of the present invention in plan view.
Figure 7B:
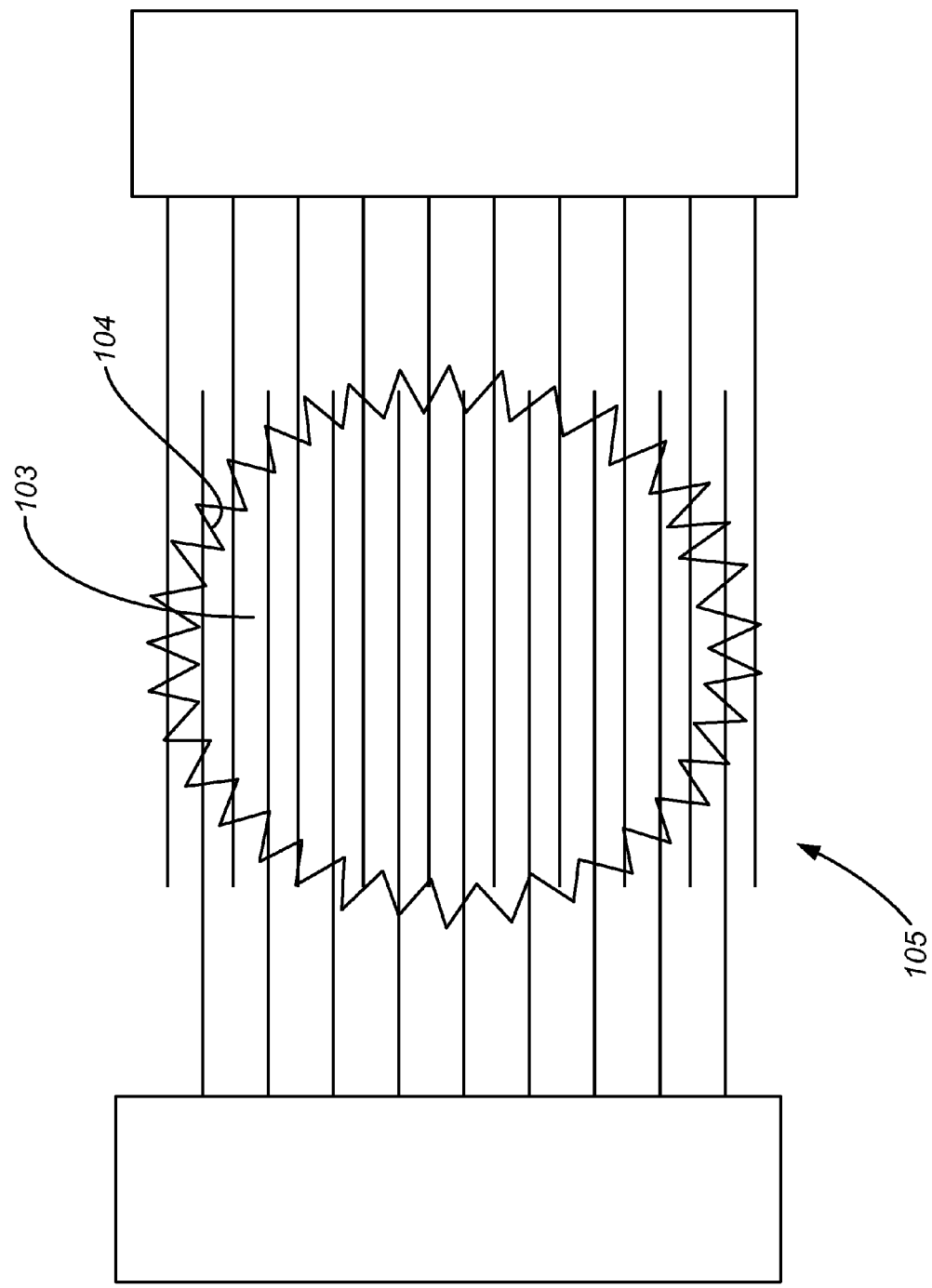
FIG. 7b shows a cut-out of an eight embodiment of the device of the present invention for performing the method of the present invention in plan view.

In FIGS. 7a and 7b, two embodiments are shown by way of example, in which interference elements are provided, which serve to increase turbulence. In FIG. 7a, reference numeral 95 designates again a transducer, which can emit a surface wave in the direction 100 in the manner previously described. A preferred holding region is designated with reference numeral 93, which can be originated, for example by modulation of the wetting characteristics. Reference numeral 101 designates turbulence structures, whose wetting characteristics corresponds to the wetting characteristics of the solid body surface outside of the preferred holding region. A liquid, which is located on the preferred holding region 93, is inhibited by these interference elements 101 to a laminar movement. Turbulences are generate, which are caused by the unfavorable wetting characteristics of the interference elements 101.

With the embodiment of FIG. 7b, the preferred holding region 103 is located in the region of the finger of the transducer 105, similar to the embodiment in FIG. 3. With the embodiment of FIG. 7b, the preferred holding region is not provided with a smooth edge, however, rather with spikes 104. A movement, which is produced with the help of the impulse transmission by the interdigital transducer on a quantity of liquid on the preferred holding region 103 is broken down by the spikes 104, so that turbulences are produced, which assist mixing.

The inference elements shown in FIG. 7 are only to be understood as an example. Other geometries of the interference elements for production of turbulence on the preferred holding region or in the depression are likewise contemplated, of course. The turbulence structures are made, for example, by etching.

Figure 8:
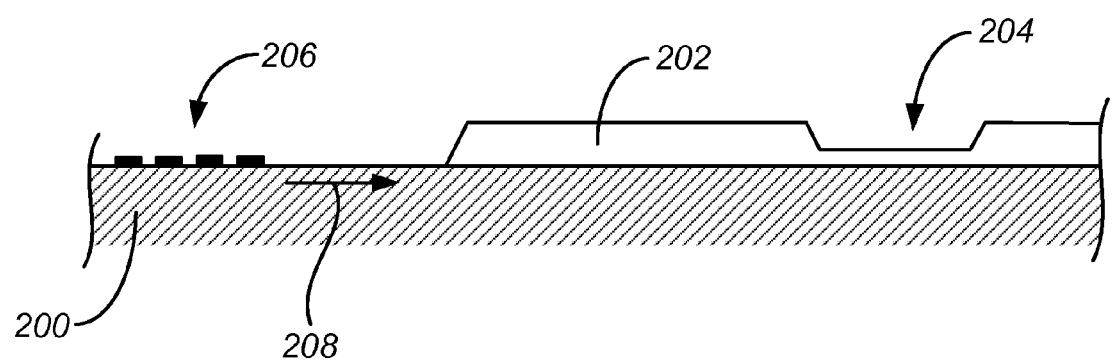
FIG. 8 shows a sectional view of a ninth embodiment of the device of the present invention for performing the method of the present invention.

FIG. 8 show the schematic section through a different embodiment of the device of the present invention. Here, reference numeral 200 designates a lithium niobate crystal as the piezoelectric solid body substrate. On a part of the crystal 200, a coating 202 made of silicon dioxide is provided, which has an etched region 204. An interdigital transducer, such as that described above, is designated with reference numeral 206. The direction 208 of a surface sound wave is designated, which can be sent out from the interdigital transducer 206, when a corresponding alternating field is applied to this. The surface sound wave widens in the piezoelectric crystal also on the silicon dioxide coating. In the etched region 204, the thickness of the silicon dioxide layer is selected to be small enough, such that it is very small relative to the wave length of a surface wave, which can be produced with the interdigital transducer 206. This means that the thickness of the coating 202 in the etched region 204 is very small relative to the finger distance of the interdigital transducer 206. A surface sound wave, which runs in the border region between the piezoelectric crystal 200 and the silicon dioxide layer 202, can be reacted with such a thin silicon dioxide layer in the etched region 204 with a quantity of liquid, which is located in the etched region 204. Such an embodiment has the advantage that silicon dioxide is very easy to etch and so a defined receptacle for the quantity of liquid can be produced. Nevertheless, the metal structure of the interdigital transducer 206 can be applied very easily with known lithographic coating methods on the piezoelectric crystal.

In addition, with all embodiments, a heating device, for example, a resistance heating, can be provided, which produces an additional mixing or temperature convection. For purposes of clarity, none of the figures shows such an embodiment.

The liquid can be applied in the active regions, for example, with a pipette robotic. Likewise, however, a supply line can be supplied (not shown). This can be a channel, through which the liquid is sent, or however, for example, with an embodiment according to one of FIG. 3 through 7, it can be a narrower strip on the solid body surface, which has the same wetting characteristics as the active region 43. Via such a supply line, liquid can be brought into the active region of the interdigital transducer 45, also, for example, by impulse transmission of a surface sound wave.

For the purposes of clarity, embodiments are shown in the figures, in which only one interdigital transducer is provided. However, multiple interdigital transducers can be provided, for example, various finger distances. The transducer, if necessary can be arranged about the reaction region. The interdigital transducer need not necessarily have a constant finger distance. With an interdigital transducer with non-constant finger distance, the wave path also is limited in the lateral direction, since the resonance conditions only can be fulfilled in a small region of the transducer.

The coatings described for the embodiments above the resonators and/or interdigital transducers are selected advantageously with a thickness, which is small or approximately the same as the wave length, which is sent from the interdigital transducers. Such a coating damps the surface sound wave mechanically not too intensely, but prevents however a capacitive coupling of the electrodes, which would lead to a reduction of the efficiency, with which the interdigital transducer converts electrical energy into acoustic energy. Such a coating preferably is insulating with a high dielectric constant, for example, made from photoresist, silicon dioxide, or silicon nitride. Such coating can be provided also with embodiments for which a coating is not explicitly shown or mentioned above.

The described embodiments are only to be understood as examples of the devices of the present invention. Of course, also other combinations of the features of the present invention can be provided. For example, a resonator structure, as is described with reference to FIG. 6, also can be provided with an embodiment, which shows a depression instead of the preferred holding region 83. Likewise, interference elements, such as those shown with reference to FIG. 7, also can be provided in embodiments in which the preferred holding region 93 or 103 is replaced by a depression, such as, for example, with the embodiments in FIG. 1 or 2. Also, embodiments, in which the surface sound wave does not impinge centrally onto the quantity of liquid can have depressions instead of the preferred holding region, as described with reference to FIGS. 4 and 5.

The invention is also not limited to realization on a chip surface. Likewise, two opposite solid body surfaces can be provided, between which the liquid is located. With such an arrangement, for example, the surface sound wave generating device can be located on the surface and the structure limiting the movement of the quantity of liquid, that is, the depression or the preferred holding region, can be located on the other solid body surface. If a small quantity of liquid contacts both surfaces, the described effect also can be achieved with this form of the invention.

All shown and described embodiments can be part of a larger system, in which multiple mixing devices are arranged on a solid body surface. On the chip surface, also other analytical or synthesis devices can be located.

The devices and methods of the present invention are suited for effective mixing of the smallest amounts of liquid, in order to provoke a reaction, for example. The device of the present invention and the method of the present invention support effectively the formation of homogenous, thermodynamic conditions in the quantity of liquid. Likewise, different quantities of liquid can be quickly and effectively mixed with one another, without being limited by diffusion. With another application of the method of the present invention, a solid, such as a powder, for example, can be applied in the reaction region. In this connection, a liquid can be brought into the active region. With the assistance of the impulse transmission of the surface sound wave, the release of the powder can be accelerated significantly. Finally, the device and method according to the present invention also can be used effectively for distribution of material, for example, biological materials, in the liquid.

Particularly advantageous, the method of the present invention can be used for analyzing the bond strength of microscopically small objects, for example, cells or bacteria on functionalized surfaces, whereby a mixing device of the present invention can be used as a cell adhesion assay.

The invention claimed is:

1. A method for mixing a quantity of liquid, comprising the steps of providing a solid body including a solid body surface comprising a reaction region and a surface sound wave generating device, applying a quantity of liquid to said reaction region, and propagating at least one surface sound wave from the surface sound wave generating device along the solid body surface into contact and interaction with the quantity of liquid, thereby mixing the liquid, wherein said surface sound wave generating device is an interdigital transducer located on the solid body surface and said reaction region is located above said interdigital transducer.

2. The method according to claim 1, wherein said reaction region is a depression.

3. The method according to claim 1, wherein said reaction region has different wetting characteristics than lateral areas surrounding said reaction region, such that the liquid is retained thereon.

4. The method according to claim 1, wherein the at least one surface sound wave is pulsed.

5. The method according to claim 4, wherein the pulse frequency of the at least one surface sound wave is selected, such that it is in resonance with an eigen frequency of the quantity of liquid on the reaction region.

6. The method according to claim 1, wherein the at least one surface sound wave is propagated such that it acts in a decentralized manner on the quantity of liquid.

7. The method according to claim 1, in which two surface sound waves are sent onto the quantity of liquid, wherein the two surface sound waves have a phase-displacement of half a wavelength.

8. The method according to claim 1, wherein said surface sound wave generating device comprises a biocompatible coating.

9. The method according to claim 8, wherein an insulating coating of the surface sound wave generating device is used as said biocompatible coating.

10. The method according to claim 8, wherein the biocompatible coating comprises photoresist, silicon dioxide, or silicon nitride.

11. A method for mixing a quantity of liquid, comprising the steps of providing a solid body including a solid body surface comprising a reaction region, a surface sound wave generating device situated on the solid body surface and spaced from said reaction region, and a resonator for a surface sound wave on said solid body surface situated underneath said reaction region, applying the quantity of liquid to the reaction region, and propagating at least one surface sound wave from the surface sound wave generating device such that the at least one surface sound wave is brought into contact and interaction with the quantity of liquid, thereby mixing the liquid.

12. The method according to claim 1, wherein interference elements are located in said reaction region for generating turbulence in the quantity of liquid.

13. The method according to claim 1, wherein multiple quantities of liquid are applied for mixing on the reaction region.

14. The method according to claim 1, wherein a material to be released on the reaction region is brought into contact with the quantity of liquid and by action of the at least one surface sound wave, is released into the quantity of liquid.

15. A mixing device for mixing a quantity of liquid, comprising a solid body surface, a surface sound wave generating device for generating a surface sound wave situated on the solid body surface, and a reaction region which is arranged to receive the quantity of liquid and situated upon the solid body surface, wherein the surface sound wave generating device is situated on the solid body surface at least partially underneath said reaction region and is an interdigital transducer.

16. The mixing device according to claim 15, wherein the reaction region is formed as a depression and the depth of the depression is less than the wave length of a surface sound wave produced by the surface sound wave generating device.

17. The mixing device according to claim 15, wherein the reaction region is designed as a depression and the surface sound wave generating device is arranged at least partially in the depression.

18. The mixing device according to claim 16, wherein the solid body surface includes a coating.

19. The mixing device according to claim 18, wherein the coating includes a silicon dioxide.

20. The mixing device according to claim 15, wherein the reaction region includes a holding region on the solid body surface, wherein the wetting characteristics of the holding region differ from the surrounding area, such that the quantity of liquid is retained on the holding region.

21. The mixing device according to claim 20, wherein the surface sound wave generating device is situated at least partially underneath the holding region.

22. The mixing device according to claim 20, wherein the surrounding area of the holding region is silanized.

23. The mixing device according to claim 15, wherein the reaction region and the surface sound wave generating device are arranged relative to one another, such that a surface sound wave generated by the surface sound wave generating device acts in a decentralized manner on the reaction region.

24. The mixing device according to claim 15, comprising at least two surface sound wave generating devices configured such that phase-displaced surface sound waves are produced in the reaction region.

25. The mixing device according to claim 15, further comprising interference elements in the reaction region.

26. The mixing device according to claim 25, wherein the interference elements include etched regions in a non-etched surrounding area or non-etched regions in an etched surrounding area.

27. The mixing device according to claim 25, wherein the interference elements include regions which are coated differently from an area surrounding said regions.

28. The mixing device according to claim 25, wherein the interference elements are formed by a non-uniform definition of the reaction region.

29. The mixing device according to claim 15, further comprising a biocompatible coating on the surface sound wave generating device.

30. The mixing device according to claim 29, wherein the biocompatible coating has different wetting characteristics from a lateral area surrounding the coating, such that the liquid preferably stops thereon.

31. The mixing device according to claim 15, additionally comprising a resonator in the reaction region, which is arranged such that the surface sound wave generated by the surface sound wave generating device resonates.

32. The mixing device according to claim 31, wherein the resonator includes periodically arranged metal coatings, whose distance corresponds to the distance between finger-like electrodes of the interdigital transducer.

33. The mixing device according to claim 31, further comprising a coating on the resonator.

34. The mixing device according to claim 15, further comprising a coating on the surface sound wave generating device.

35. The mixing device according to claim 33, comprising a thickness, which is smaller or essentially the same as the wave length of the surface sound wave produced by the surface sound wave generating device.

36. A method according to claim 1, wherein the quantity of liquid comprises microscopically small objects and the method further comprises the step of counting the number of the objects adhered to the a surface on the solid body during or after the step of propagating the at least one surface sound wave, thereby analyzing the bond strength of the objects.

37. The method according to claim 36, wherein the quantity of liquid is a nutritive solution and the objects are cells or bacteria.

38. The method of analysis according to claim 36, in which the surface is functionalized in at least one sub-area.

39. A mixing device for mixing a quantity of liquid, comprising a solid body surface, a reaction region arranged upon the solid body surface, a surface sound wave generating device arranged on the solid body surface and spaced from from said reaction region and is an interdigital transducer, and a resonator situated on said solid body surface and underneath said reaction region.

40. The mixing device according to claim 39, wherein said interdigital transducer includes oppositely-arranged electrodes each comprising finger-like electrode structures engaging one another.

41. The mixing device according to claim 39, wherein the resonator includes periodically-arranged strips of metal coatings at a distance from each other.

* * * * *